United States Patent [19]

Lines

[11] 4,237,896
[45] Dec. 9, 1980

[54] IMMOBILIZING ANIMALS

[75] Inventor: Lancelot H. Lines, Adelaide, Australia

[73] Assignees: Senil Nominees Pty. Ltd, Adelaide; Australian Merino Wool Harvesting Limited, Perth, both of Australia

[21] Appl. No.: 62,640

[22] Filed: Aug. 1, 1979

Related U.S. Application Data

[63] Continuation of Ser. No. 920,239, Jun. 29, 1978, abandoned, which is a continuation-in-part of Ser. No. 900,139, Apr. 26, 1978, abandoned, which is a continuation of Ser. No. 708,934, Jul. 27, 1976, abandoned.

[51] Int. Cl.³ .............................................. A61N 1/32
[52] U.S. Cl. .............................. 128/419 R; 128/421; 128/785
[58] Field of Search ............... 128/1 C, 421, 422, 741, 128/784, 785, 787, 799, 800, 802, 642; 17/1 E

[56] References Cited

U.S. PATENT DOCUMENTS

| 1,935,138 | 11/1933 | Windisch | 128/799 |
| 3,523,538 | 8/1970 | Shimizu | 128/785 |
| 3,612,060 | 10/1971 | Colyer | 128/422 |
| 3,682,162 | 8/1972 | Colyer | 128/741 |
| 3,800,784 | 4/1974 | Kiszel et al. | 128/642 |
| 3,897,789 | 8/1975 | Blanchard | 128/422 |
| 3,900,020 | 8/1975 | Lock | 128/422 |

FOREIGN PATENT DOCUMENTS 1365478 5/1964 France .................................... 128/1 C Primary Examiner—William E. Kamm
Attorney, Agent, or Firm—Kinzer, Plyer, Dorn & McEachran

[57] ABSTRACT

An animal can be immobilized by passing a pulsed electric current through the animal's muscles to cause a state of tetany in the muscles while leaving the organs in a relaxed condition.

9 Claims, 5 Drawing Figures

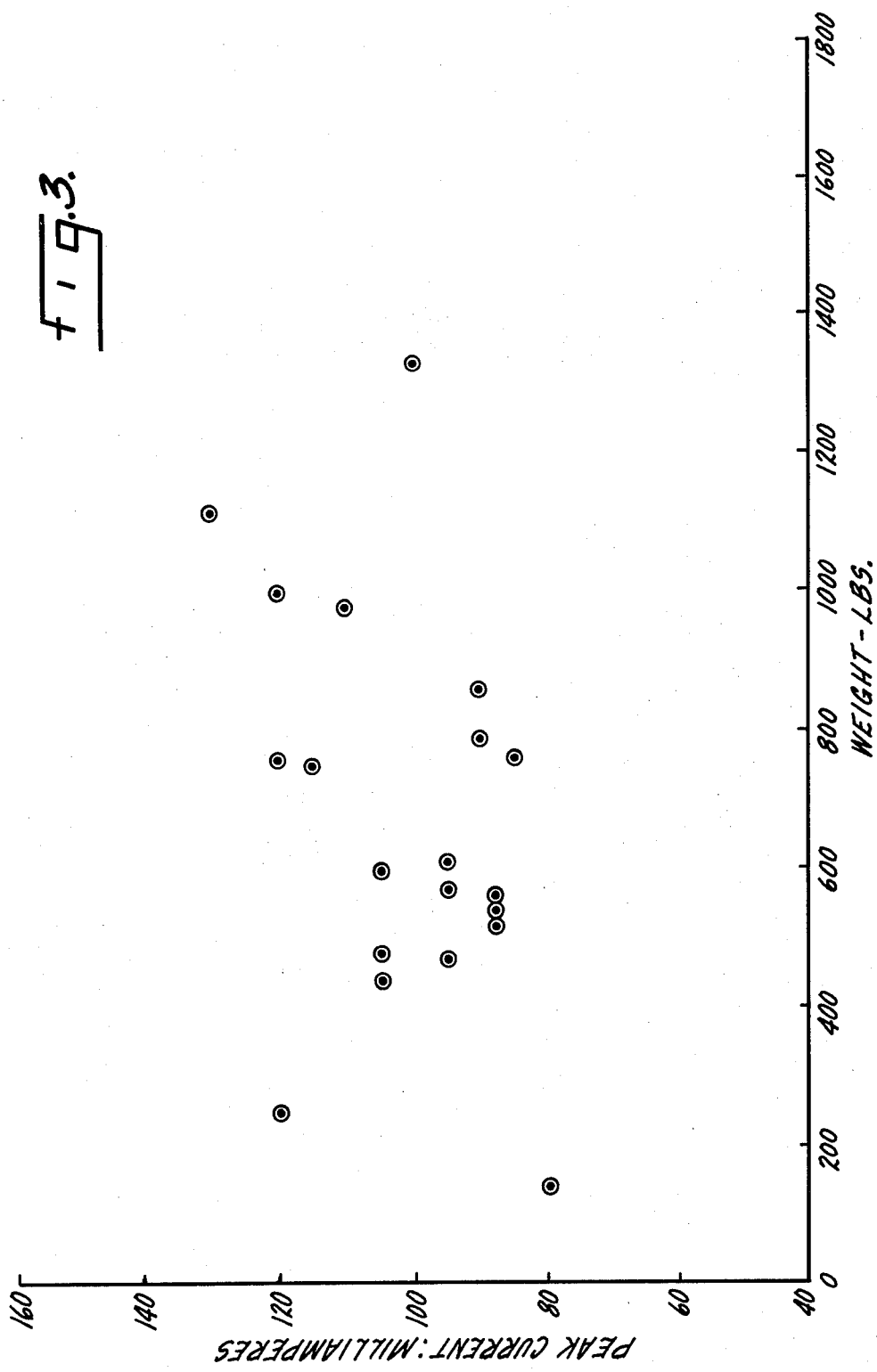

IMMOBILIZING ANIMALS

REFERENCE TO RELATED APPLICATION

This is a continuation of application Ser. No. 920,239, filed June 29, 1978 now abandoned is a continuation-in-part of application Ser. No. 900,139 filed Apr. 26, 1978, now abandoned the latter being a continuation of application Ser. No. 708,934, filed July 27, 1976, now abandoned.

This invention relates to a method of and means for handling animals, and in particular to the handling of animals such as sheep, cattle and other animals for handling or veterinary purposes.

In animal husbandry there is often the requirement to restrain or immobilize an animal for veterinary purposes, or in the case of a sheep, to allow shearing to take place. Conventionally this has been by some mechanical means for holding and restraining the animal, or in the shearing of sheep to manually restrain the animal by the shearer while the shearer himself carries out the shearing operation. With animals such as wild beasts, the animal is drugged and anaesthetised, but this is a relatively slow process, for it takes time for the drug to anaesthetise the animal, and also after the treatment the animal takes a degree of time in order to recover.

The present invention relates to an improved method and means of immobilizing and handling animals, and is concerned with an electrical method and apparatus for carrying out this manner of handling animals.

BACKGROUND OF THE INVENTION

In the field of electro-treatment of animals and humans, there is disclosed in the U.S. Pat. No. 535,905 dated Mar. 19, 1895; "A Method of and Apparatus for Obtaining Nerves", granted to Horton W. P. and Jones A. B. Also U.S. Pat. No. 2,866,461, granted Dec. 31, 1958 to K. Suzuki, for "Apparatus for Producing Electric Anaesthesia" relates to apparatus for the electro-anaesthesia where the patient is anaesthetised in the area of the operation to be performed. Also U.S. Pat. No. 3,083,463, dated Apr. 2, 1963, to Brooks B. and Sylvane A. A., relates to "Dental Drilling and Apparatus Therefore".

Also it is known that electro-anaesthesia on large animals can be carried out, such as discussed in the article by C. E. Short, D.V.M. in Journal of American Veterinary Medical Association, Volume 145, No. 11, entitled "The Application of Electro-Anaesthesia on Large Animals". This discusses the techniques of total anaesthesia by passing an electric current through or around the head of the animal and results in total relaxation of the animal.

SUMMARY OF THE INVENTION

By research it has been discovered that animals can be immobilized by using an electrical current flow of low voltage and small currents, and of a particular frequency to form a pulse, with a relatively short pulse width, with a relatively large duration between the pulses, thus causing the muscles to be in a rigid state, or state of tetany.

This has a definite advantage in the shearing of sheep, where the sheep can be rigidly immobilized in a desired position of the limbs, this allowing a purely mechanical shearing of the sheep to take place.

Also with other animals, such as cattle, horses and even wild animals, the animals can be immobilized while in a standing position, to allow veterinary and animal husbandry work to be carried out.

BRIEF DESCRIPTION OF THE DRAWINGS

FIG. 3 is a chart of the currents required for various weights of cattle;

DESCRIPTION OF THE PREFERRED EMBODIMENT

Figure 1:
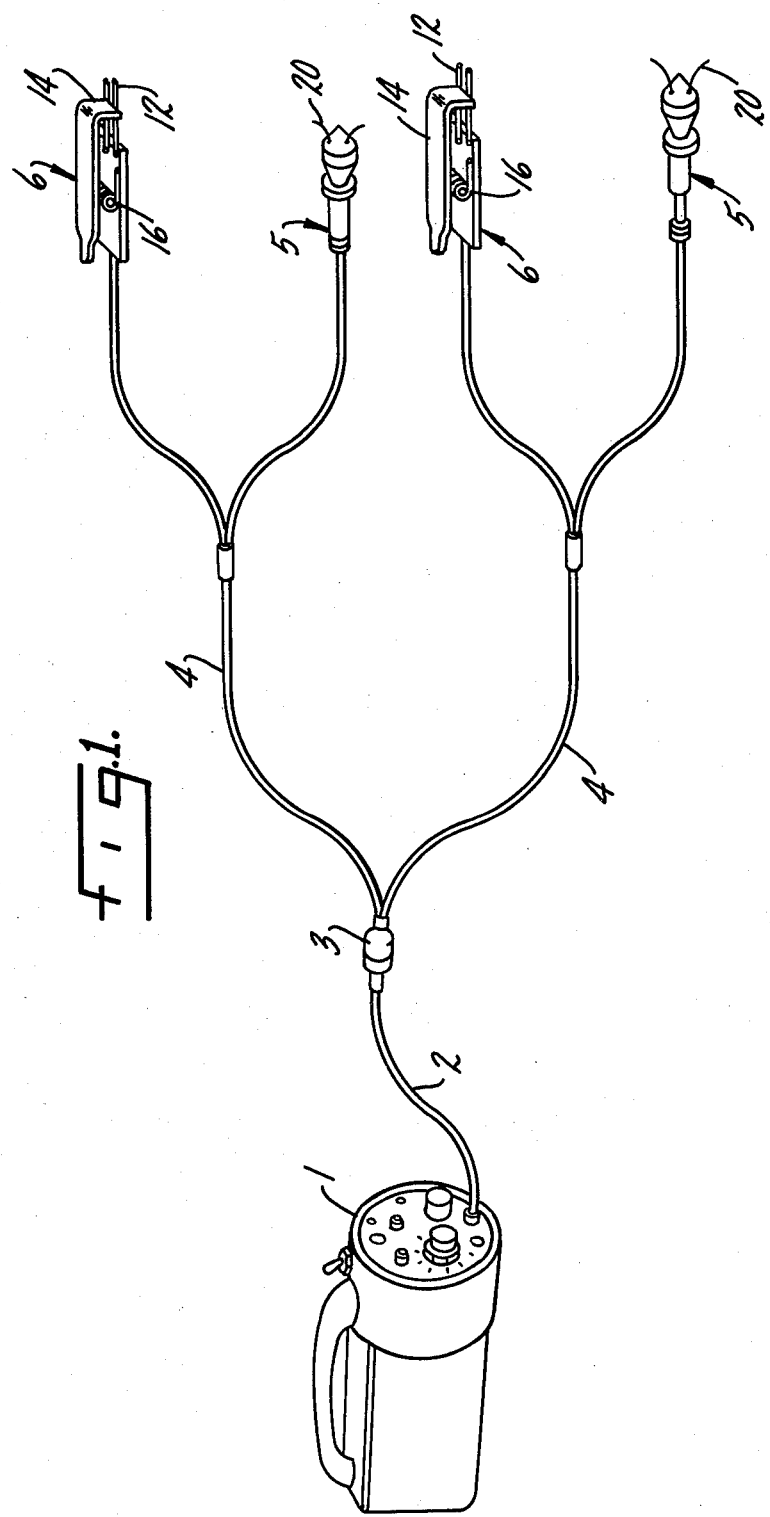
FIG. 1 is a diagrammatic illustration of the immobilizer.

It has been determined that the immobilization of animals can be carried out by an electric current, having a potential of 40 v. and a current in the vicinity of 50 milliamperes will immobilize a sheep, and that about 100 milliamperes is required for immobilizing cattle, the current being pulses of 50 Hertz, each pulse being of 1 millisecond and spaced 20 milliseconds apart.

Research work to date has shown that a current having a constant amplitude driven by a low voltage high impedance source is safer for operators to use, and this can be achieved if the electrodes which are attached to the animal are so designed that they pierce the skin at the point of application, so as to make contact with the ionized fluids under the skin and/or in the muscular tissue of the animal.

Indeed the work has shown that it is the magnitude of the current for a particular wave characteristic, frequency and points of application that determines the immobilizing effect, rather than the voltage required to drive this current.

The skin of most animals is comprised of horny (dry cell) outer layers beneath which is found a layer of fatty tissue, and under this fatty tissue layer exist the ionized body fluids and muscular tissue.

The electrical resistivity of the horny outer layers in the adjacent fatty tissues is high, relative to the electrical resistivity of the ionized body fluids and muscular tissue.

If electrodes were simply placed or clipped on the outer skin, most of the voltage would be consumed in driving the required current through the horny outer layers and adjacent fatty tissues, while only a small part of this voltage would be consumed in driving the required current through the ionized body fluids and muscular tissue within the animal.

On the other hand, if the electrodes pierce the skin first and make contact with the ionized body fluids and muscular tissue, relatively low voltages, safe for the human operators to handle, would be required to drive the immobilizing currents through the animals.

It was also found that the resistance between the electrodes to some extent, depended upon the area of contact that the electrodes made with the ionized body fluids and muscular tissue, so that as this area increased the resistance between the electrodes decreased.

In a particular application on cattle and sheep using a pulsed current source of 50 Hertz frequency, and a pulse width of 1 millisecond whose amplitudes could be controlled accurately between 0 and 1 amp. and whose voltage did not exceed 40 volts, the largest animals were easily immobilized without detrimental effect to the animals or electrical hazard to the human operators on application of the electrodes.

In a particular design of the electrodes, a spring-actuated plunger incorporated in an insulating housing and operated by a trigger mechanism which can be reset, contains on one end of the plunger either barbed, straight or current needles, depending on the requirement, connected to a conducting strip or rod which makes contact with the current source on operation of the plunger. The barbed or curved needles ensure that the electrodes remain attached to the animals even though they may make a violent movement on insertion of the electrodes.

It is not intended that the electrodes be limited to the above design, but they may have various shapes or sizes and be applied in any manner provided that they preferably contact the ionized body fluids and/or muscular tissue under the skin of the animals.

The invention is designed to immobilize cattle and other animals in a quick, safe manner so that operations such as shearing, dehorning, castration, etc., and other forms of surgery may be carried out in the field or elsewhere in an efficient manner, with the minimum of physical effort required to restrain the animal. The animal is immobilized by the passage of the small electric current through the nerve and the muscle tissue thus causing tetany, that is the contraction of the muscles, thus immobilizing the animal and effecting its nervous system in such a way that the animal is not conscious of any pain when the correct current is applied.

No ill effects have been observed to date on the many experiments carried out on animals, but care must be taken to ensure that the current applied is not so great that it prevents the animal breathing for a period long enough to produce asphyxia. it is felt that the immobilization can have a therapeutic value on the animals.

The electronic unit is equipped with a warning device which makes a buzzing sound when the electrodes are not connected, or when the electrodes are making a poor connection on the animal. This is considered necessary as the animal will recover from its immobilized state within a few seconds of removing the required immobilizing current.

Turning now to FIG. 1, this shows the electronic unit 1 having an outward lead 2 connected by a plug 3 to a pair of electrode leads 4. Each lead 4 is connected in this example, to two electrodes, a dart electrode 5 and a clip electrode 6. For large animals such as cattle, the dart 5 is used first to immobilize the animal, and then the clip electrode 5 can be inserted in the desired location.

For the immobilization of sheep, it is not required to use the dart electrodes, but the clip electrodes can be applied directly to the sheep.

Figure 2:
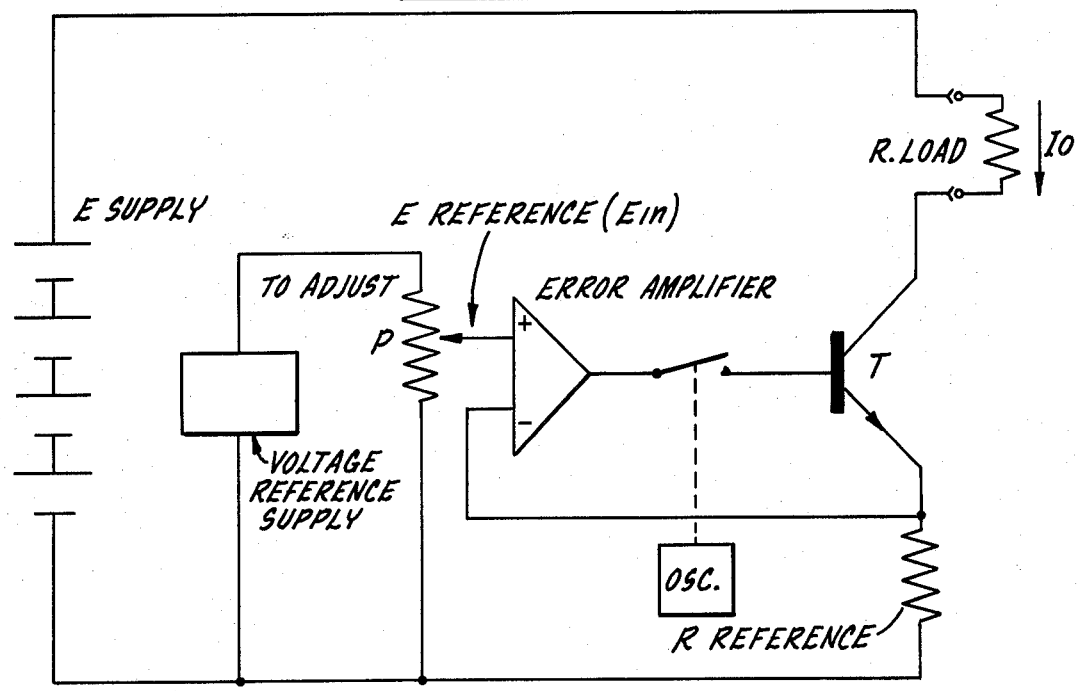
FIG. 2 is a circuit diagram of the immobilizer.

FIG. 2 shows a schematic circuit of the immobilizer, where the output current Io is equal to Ein divided by the reference resistance (R reference). The error amplifier and the series transistor T maintain the outward current Io at a level such that the voltage drop across the reference resistance (R reference) is equal to Ein. The voltage from the reference voltage supply is passed to an adjustable potentiometer P, which provides adjustment of Ein such that Io can be adjusted from 0 up to 0.3 amperes. To pulse the outward current the series transistor T is turned on and off by an oscillator and transistor switch.

The oscillator is adjusted to such that the output pulse width is 1 millisecond and the pulses occur at 50 Hertz, and the output current is continuously adjustable with a resolution of better than 1 milliamp. The voltage compliance of the output is 40 volts, and this can be readily changed.

FIG. 3 shows a chart of tests which have been carried out on cattle, plotting animal weight against peak current applied to the animals. Experiments have shown that while it is initially assumed that a variation in current required would correlate to the animal weight, that this is not so, for it is shown in the graph that the general level of immobilization is between 80 and 300 milliamperes. Smaller animals often require greater current flow than larger animals, but generally it has been noticed that younger animals require an increased current flow for immobilization.

While no direct correlation is yet available, it may well be that there is a correlation between the vitality or energy of the animal and current flow.

It has been found that with certain breeds of cattle, for example BOS TAURUS which is essentially an English breed, that current values as shown in FIG. 3 are obtained. However with other breeds such as the tropical breed BOS INDICUS, that higher currents up to 300 milliamperes are required to immobilize the animals.

For the immobilization of cattle, the initial setting, it is estimated, should be 100 milliamperes, and the current then increased or decreased according to the state of immobility induced in the particular animal. The initial effect is for the animal to stiffen up to such an extent that breathing is temporarily arrested. Between 1 and 2 minutes however, the animal commences to breathe again, which is indicated by the heaving of the chest wall and flanks.

If signs of breathing are not evident after this time, the current setting should be reduced quickly to allow the animal to breathe, but not so far as to entirely reduce the stiff condition of the animal.

Animals have been kept immobilized up to twenty minutes in experiments performed so far, without any apparent ill effects. it will be noticed however, that after several minutes an animal tends to accomodate itself to the current levels being used, and a further one or two fine increments of the current may be necessary to maintain the immobile state.

Where dehorning, castration or some other operation characteristic of animal husbandry is to be performed on the animal, it is preferable to apply a heavier current than the threshold level for immobility, and to perform the operation without waste of time, rather than applying a current just over the threshold level and having to increase the current to maintain their immobility.

The animals recover immediately, and sheep have begun grazing within minutes of being removed from the immobilizing current, and all animals show no signs of distress after the immobilization.

While the invention is particularly adapted for completely immobilizing an animal by applying the current from head to tail of the animal, the animal may be positioned as desired, and by slightly reducing the current, repositioning the animal in the desired position, and then raising the current to cause the animal to again stiffen. The animal can be held in any position.

Also various portions can be held as desired so that by applying the current to portions of the body such as a leg, the leg muscles can then be held in any desired position. For example, by applying the current to a rear leg of a horse, that leg is immediately held up by the passage of the current through the muscles, the leg being held in a position whereby shoeing or other treatment can be carried out on that leg or hoof. Thus by applying the electrodes to the desired muscles, the leg can be held as positioned.

Thus it has been found that various parts of the animal may be in a state of tetany while other parts may be relaxed. Thus it is possible to stiffen the major muscles, while the organs are relaxed, for example, the internal organs, testes and mammary glands.

Cows while being immobilized have been milked substantiating the fact that various organs can be relaxed.

It has also been found on investigation, that while the optimum current to be applied is a pulse of a short time interval such as 1 millisecond with a large period, say 20 milliseconds, between each pulse, it has been found that restraint and immobilization can be obtained by the application of pulses and wave forms other than those described.

Thus it has been found that by the application of an alternating current of even sinusoidal wave form is satisfactory to restrain an immobilized animal. Also other wave forms such as a square wave, a triangular wave, and the application of both unipolar and bi-polar forms can be utilized to restrain the animal. Thus it is to be realised that the invention is not limited to the specific pulse formation as described as being the optimum form, where it has been found that other wave forms can produce satisfactory results without detrimental affects to the animal.

In this respect also it has been found that a pulse or alternative wave form is not essential but that restraint can be applied by the application of a direct current to the animal, although it has been found that the pulsating form is preferred.

In a further application of the invention micro switches may be included in the line of the clip, so that this forms an additional safety feature. Thus it is possible now to apply the clips without any electrical supply being provided to the clips themselves, and the controls can be adjusted to give a minimum voltage of the like, so that on switching on the micro switches at the clips, the animal can be immediately restrained, and then the control can be adjusted to give the required degree of immobilization.

This is of advantage, for otherwise the animal can sometimes be affected by a small electrical current flow which would be annoying or aggravating to the animal, which may struggle before the control is adjusted to achieve the desired degree of immobilization, and hence, with the use of the micro switches the animal can be immediately and instantaneously immobilized or restrained without feeling any affects or build-up to this immobilizing degree.

The invention is of particular importance also for immobilizing sheep to allow fully automated shearing operations to take place.

Thus the immobilizing current may itself, be utilised in assisting the positioning of a cutter by sensing means. For example, this current through the animal produces a field which can be sensed by a sensing coil, and also an additional high frequency can be superimposed on the immobilizing current, and this high frequency field can be sensed.

Furthermore a tuned coil can be used to sense the proximity of the contour, the tuned coil being insulated, so that the proximity of a surface causes the coil to be detuned.

Also other proximity sensors can be used, such as capacitance sensing, force, sensing or even force sensing.

Thus the invention can be applied to the immobilization of animals in general, and while it is particularly adapted to the use of animals of a domestic or agricultural nature, it is to be readily seen that the invention is also applicable to beasts and animals of any kind, and for example, by utilising a device with a portable power source, and some form of portable race or crush that animals in the field or even in the wild state can be driven into such a race or crush and then immobilized for treatment, shearing or any other desired purpose.

There is no doubt that a need exists to temporarily immobilize animals for all manner of different purposes. The use of ropes, races, crushes, head bails and other various mechanical contrivances are all attempts to achieve this effect. Similarly, drugs in the form of tranquilizers and anaesthetics are also an attempt to achieve this effect and, additionally of course, they suppress pain. All these various devices achieve a certain degree of success and all have a number of limitations and/or side effects. In the case of mechanical restraints, there is always some random kicking or other body movement and anaesthetics are both time-consuming and can also result in difficulties during the recovery period.

One feature of novelty is that whereas prior workers approached the problem by the various means mentioned above, the physiological state of the animal under the present invention is manipulated to achieve these desired effects:

(a) the muscles used by the animal for movement (i.e., the major skeletal muscles) are all controlled at the same time (i.e., simultaneously) so that there can be no random kicking or head tossing, (b) the animal is allowed to breathe satisfactorily and remain conscious, (c) the animal recovers movement instantaneously when the control is removed, (d) the transmission of pain impulses along the nerve fibres to the brain are blocked.

These conditions are effected for the purpose of immobilizing an animal to allow the best performance of husbandry procedures. Control of a single muscle or even groups of muscles on an extremity does not give the degree of immobilization required for the animal husbandry procedures undertaken. One particular instance of such a procedure is the automated shearing of sheep where it is necessary not only to keep the animal absolutely still, but also to have the skin reasonably tight over the skeletal muscles. This effect allows the wool to be "combed" easily during wool cutting.

Also, the method disclosed incorporates findings which are considered both novel and non-obvious from any known or published art. These include:

1st Finding

That inducing a tetanic contraction into the major skeletal muscles of an animal adjacent the spine, all at the same time, (i.e., simultaneously) prevents the animal from moving (i.e., immobilized) to the extent that animal husbandry procedures can be performed effectively.

Note: (i)
There is no need to "shock" or stun the animal which in reality represents an approach to the threshhold of outright electrocution.

2nd Finding

That establishing a pulsed D.C. electric current flow to the head and tail areas of an animal adjacent to the spine, induces a tetanic contraction into all of the major skeletal muscles at the same time (i.e., simultaneously) without evidence of pain normally sustained when tetanic spasm of a single muscle occurs; and, on stopping this current flow, the tetanic contractions are immediately removed.

Figure 4:
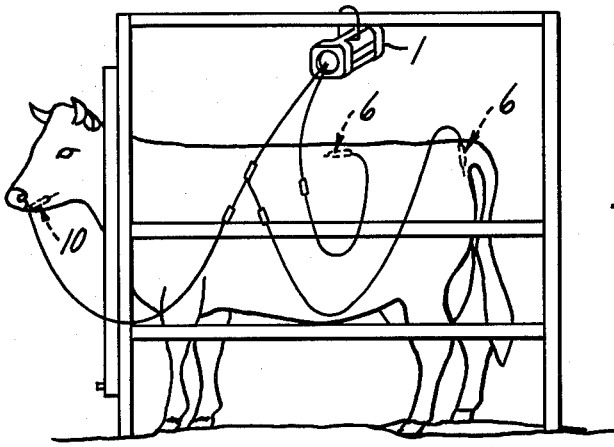
FIGS. 4 and 5 show typical application of the electrodes to a cow.
Figure 5:
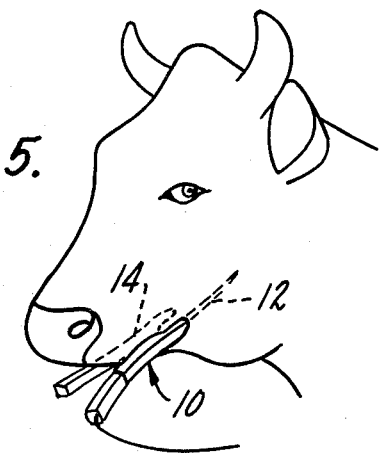

Note:

(i) The present finding in relation to the positioning of necessarily only two electrodes to achieve the desired condition is considered new and of advantage. Further, the use of a third electrode 10, FIGS. 4 and 5, which is connected in parallel to one of the other two electrodes, enables the distribution of the current flow to be readily altered along the spine so that different degrees of tetany are obtained in the hindquarters and forequarters. This is of advantage in long animal husbandry procedures in that breathing can be assisted by lessening tetany in the forequarters, while maintaining high tetany of the hindquarters to maintain immobilization. The third electrode 10 need not necessarily incorporate a needle 12 because the metal clip 14 on the inside of the mouth contacts the salivary fluid serving as a conductor fluid.

3rd Finding

That definite levels of the known type of tetanising current are required to establish sufficient simultaneous tetanic contraction of the major skeletal muscles to render the animal immobile, but yet not to cause contraction which prevents breathing.

Note:

(i) Too low a current level does not immobilize the animal and can cause it to become excited. Too high a current level does not allow the animal to breathe.

4th Finding

That the use of electrodes which pierce the skin in a manner to allow a calculated area of the electrode to contact the ionized body fluids and which are retained in this position by a spring clamp, results in low voltage potentials up to 40 volts D.C. maximum being required to establish the current level necessary to provide simultaneous tetanic contraction of the major skeletal muscles.

Notes:

(i) The apparatus comprising the electronic circuits of the immobilizing unit is designed to produce up to 40 volts D.C. maximum under normal operating conditions. However, in a worst fault condition, the maximum voltage which can exist across the two electrodes is 55 volts D.C. which is considered safe for human operators unless, by a deliberate act, both electrodes are made to pierce the skin.

(ii) The needles 12 are sharp and are inserted parallel to the skin surface enabling the clamping portion 14 (via biasing coil spring 16) to grip on the outer skin surface which is forced onto the needle part of the electrode to ensure good electrical contact while providing a positive mechanical retention of the needle.

(iii) The dart electrodes 5 may or may not be necessary and therefore may be omitted. Each incorporates a pair of curved, sharp-ended needles 20 intended to be implanted by a quick thrust into restive animals. Also, the clip-on electrodes 6 may have one electrode needle instead of two and the spring clips themselves may be in the form of common automotive battery (accumulator) cable clips such as shown for the third or mouth clip 10, FIG. 5, which, it will also be noted, only has one needle.

I claim:

1. A method of producing temporary immobilization of an animal undergoing animal husbandry without rendering the animal unconscious, including the step of implanting electrodes subcutaneously and clipping them to the hindquarters and forwardly thereof along the spine of the animal, the electrodes piercing the skin and the fatty tissue beneath thereby to contact the ionized fluids beneath the skin allowing a low voltage to be used, subjecting the electrodes to a current flow driven by a potential of up to about 55 volts maximum to produce immobilizing simultaneous muscular tetanic contraction in the animal and, while the animal is thus immobilized, performing animal husbandry on the animal.

2. The method of claim 1 including the additional step of clipping a third electrode to the mouth of the animal, said third electrode being connected in parallel to one of the other two electrodes.

3. A method of immobilizing animals as defined in claim 1 or 2 characterized in that the current is comprised of spaced pulses, the duration of each pulse being small in relation to the spacing between the pulses.

4. A method of immobilizing animals as defined in claim 3, characterized in that the frequency of the pulses is about 50 Hertz.

5. A method of immobilizing animals as defined in claim 4, characterized in that each pulse is about 1 millisecond in duration.

6. A method of immobilizing sheep as defined in claim 1, characterized by applying a current flow of about 40 to 60 milliamperes.

7. Apparatus for immobilizing animals to cause a state of muscular tetany, the apparatus including an electric power source with about 55 volts maximum potential available and current flow up to about 300 milliamperes to effect tetany in cattle and sheep, electrodes connected to the power source, said electrodes being characterized by (1) needles with sharp ends to be implanted subcutaneously in the animal in combination with (2) spring-biased clips for clamping the hide of the animal to retain the needles.

8. Apparatus according to claim 7 characterized by means for oscillating the power voltage at the rate of about 50 Hertz in pulses of about 1 millisecond duration.

9. A method of immobilizing cattle as defined in claim 1, characterized by applying a current flow of about 80 to 300 milliamperes.

* * * * *